(12) United States Patent
Hutton et al.

(10) Patent No.: US 7,778,849 B1
(45) Date of Patent: Aug. 17, 2010

(54) DATA ACCURACY FILTER FOR INTEGRATED EMERGENCY MEDICAL TRANSPORTATION DATABASE SYSTEM

(75) Inventors: Kevin C. Hutton, Solana Beach, CA (US); Scott J. Jones, Escondido, CA (US)

(73) Assignee: Golden Hour Data Systems, Inc., San Diego, CA (US)

( * ) Notice: Subject to any disclaimer, the term of this patent is extended or adjusted under 35 U.S.C. 154(b) by 1782 days.

(21) Appl. No.: 10/007,644

(22) Filed: Nov. 6, 2001

Related U.S. Application Data (60) Provisional application No. 60/246,310, filed on Nov. 6, 2000.

(51) Int. Cl.
*A61B 5/00* (2006.01)
*G06F 19/00* (2006.01)

(52) U.S. Cl. .................. 705/3; 705/2; 705/4; 711/103; 713/2; 345/629

(58) Field of Classification Search ................. 705/2–4; 711/103; 713/2; 345/629
See application file for complete search history.

(56) References Cited

U.S. PATENT DOCUMENTS

| | | | |
|---|---|---|---|
| 1,873,126 A | 8/1932 | Hugershoff | |
| 2,977,177 A | 3/1961 | McLaughlin et al. | |
| 3,921,318 A | 11/1975 | Calavetta | |
| 4,221,404 A | 9/1980 | Shuffstall | |
| 4,236,332 A | 12/1980 | Domo | |
| 4,814,711 A | 3/1989 | Olsen et al. | |
| 4,819,053 A | 4/1989 | Halavais | |
| 4,858,121 A | 8/1989 | Barber et al. | |
| 5,122,959 A | 6/1992 | Nathanson et al. | |
| 5,146,439 A | 9/1992 | Jachmann et al. | |
| 5,283,829 A | 2/1994 | Anderson | |
| 5,327,341 A | 7/1994 | Whalen et al. | |
| 5,465,206 A | 11/1995 | Hilt et al. | |
| 5,483,443 A | 1/1996 | Milstein et al. | |
| 5,508,912 A | 4/1996 | Schneiderman | |

(Continued)

FOREIGN PATENT DOCUMENTS

JP     01319861 A     12/1989

(Continued)

OTHER PUBLICATIONS

Schriewer, "Airborne Ambulance Saves Precious Time," Tulsa World, May 22, 1996, pp. 1-2.

(Continued)

*Primary Examiner*—Gerald J. O'Connor
*Assistant Examiner*—Linh Le
(74) *Attorney, Agent, or Firm*—Manuel F. de la Cerra (57) ABSTRACT

An integrated medical database system for the emergency medical transportation business. The system includes a dispatch module, clinical module, administration module and billing module. Each module may communicate data with one or more of the other modules to form a system incorporating data sharing, thus achieving an end-to-end automation of emergency medical care accounting. Internal consistency checks using specific libraries of modifiable data rules are performed by the system to ensure that proper treatments are performed according to a chosen diagnosis. The system includes a demographic data accuracy filter operating on patient data prior to the billing module.

14 Claims, 4 Drawing Sheets

U.S. PATENT DOCUMENTS

| | | | |
|---|---|---|---|
| 5,544,044 | A | 8/1996 | Leatherman |
| 5,550,976 | A | 8/1996 | Henderson et al. |
| 5,619,991 | A | 4/1997 | Sloane |
| 5,734,706 | A | 3/1998 | Windsor et al. |
| 5,761,278 | A | 6/1998 | Pickett et al. |
| 5,805,670 | A | 9/1998 | Pons et al. |
| 5,867,821 | A | 2/1999 | Ballantyne et al. |
| 5,874,897 | A | 2/1999 | Klempau et al. |
| 5,900,883 | A | 5/1999 | Crucs |
| 5,911,132 | A * | 6/1999 | Sloane ............... 705/3 |
| 5,940,013 | A | 8/1999 | Vladimir et al. |
| 5,974,355 | A | 10/1999 | Matsumoto et al. |
| 6,029,144 | A | 2/2000 | Barrett et al. |
| 6,044,323 | A | 3/2000 | Yee et al. |
| 6,106,459 | A | 8/2000 | Clawson |
| 6,117,073 | A | 9/2000 | Jones et al. |
| 6,151,581 | A * | 11/2000 | Kraftson et al. ......... 705/3 |
| 6,324,516 | B1 | 11/2001 | Shults et al. |
| 6,438,533 | B1 * | 8/2002 | Spackman et al. ....... 706/45 |
| 6,529,876 | B1 * | 3/2003 | Dart et al. ............ 705/4 |
| 6,542,905 | B1 * | 4/2003 | Fogel et al. ......... 707/200 |
| 6,543,905 | B1 * | 4/2003 | Adams et al. ........ 362/122 |
| 6,704,720 | B2 * | 3/2004 | Arai et al. ............ 707/3 |
| 6,725,209 | B1 * | 4/2004 | Iliff ................. 706/45 |
| 6,751,630 | B1 | 6/2004 | Franks et al. |
| 6,785,410 | B2 | 8/2004 | Vining et al. |
| 6,868,074 | B1 * | 3/2005 | Hanson ............. 370/328 |
| 6,915,265 | B1 | 7/2005 | Johnson |
| 7,233,905 | B1 | 6/2007 | Hutton et al. |
| 2001/0034618 | A1 * | 10/2001 | Kessler et al. ......... 705/4 |
| 2002/0004729 | A1 | 1/2002 | Zak et al. |
| 2002/0010679 | A1 | 1/2002 | Felsher |
| 2002/0065099 | A1 | 5/2002 | Bjorndahl |
| 2002/0120846 | A1 | 8/2002 | Stewart et al. |
| 2003/0036683 | A1 | 2/2003 | Kehr et al. |
| 2003/0093320 | A1 | 5/2003 | Sullivan |
| 2005/0240613 | A1 | 10/2005 | Logan |

FOREIGN PATENT DOCUMENTS

| | | |
|---|---|---|
| WO | WO 03102726 | 12/2003 |

OTHER PUBLICATIONS

Hudson, "Attorneys Fear Patient Transfer Claims in Malpractice Cases," Hospitals, Apr. 5, 1991, vol. 65, issue 7, pp. 44-48.
Segroves, "Navigation systems aids medical flights Bad weather landings are now possible at hospitals," News Sentinel, Aug. 7, 1994, pp. D7-8.
Spencer, Thomas, "Contracting for helicopter emergency transport services," Healthcare Financial Management, Aug. 1993, pp. 67-72.
www.aeromed-software.com, Feb. 5, 1998.
Public Law 104-191, Health Insurance Portability and Accountability Act of 1996, published Aug. 21, 1996, located at <http://aspe.hhs.gov/admnsimp/pl104191.htm>.
Wyoming Medicaid Provider Manual Billing Manuals, Mar. 1, 1999. Section on HCFA 1500, chapters 4 (pp. 4-4, 4-7, and 4-54 in particular) and 9 (pp. 9-11 to 9-13). Section on Transportation, chapter 3 (3-12 to 3-22 in particular) and Appendices (C, D).
Wyoming Medicaid Provider Manual Billing Manuals, Mar. 1, 1999. Section on HCFA 1500, chapters 4 (pp. 4-4, 4-7, and 4-54 in particular) and 9 (pp. 9-11 to 9-13). Section on Transportation, chapter 3 (3-12 to 3-22 in particular) and Appendices (C, D).
Obertots, Richard M.; "Report on EMS Software Providers: Interfacing Modules; The Industry Standard" *ThinkThrough Tools, LLC*, Jul. 2007, 9 pages.
SweetTalk Newsletter, Sweet Computer Services Inc. Vo. 2(3), Aug. 1993, 10 pages.
Various Sweet Computer Services, Inc.'s advertisements and brochures for SweetSoft™ software, 1990, 21 pages.
Lancet Technology, Inc. "Rescue One, The Complete EMS Database Management Solution" Brochure, 8 pages.
Flightstar: "A System Designed for Dispatchers, by Dispatchers" Flyer, 2 pages, 1989.
Computing Technologies for Aviation, Inc.'s Medical Air Transport System fact sheet, Sep. 1992, 2 pages.
Droege Computing Services, Inc. "Computing Services Emergency Flight System", Handout 1 pages.
EMS Consultants Ltd. "The Ultimate in EMS Software", Brochure 30 pages.
EMS Expert @P-Docs Flyer 2 pages.
Westech System brochure 7 pages.
LifeLink III reports, printed Sep. 6, 1988, 14 pages.
Arec Data Management Systems Flyer 3 pages.
Iris Product and Services Handout 2 pages.
DataWest's Air-Ops Version 2.1 Software Manual 15 pages.
LiFlex Computer Aided Dispatch System Flyer, 1991 or prior, 2 pages.
UCS Fire Rescue Incident Report, 1994, 10 pages.
The Northern Virginia Sun Article, dated May 10, 1993, 2 pages.
Weekly Business Article, dated Feb. 14, 1994, 1 page.
UCS The EMS Commander Brochure 8 pages.
Fireline Brochure 4 pages, printed Jul. 20, 2007.
UCS Pen Based Solutions for EMS Brochure 4 pages.
OuterLink Web 4 pages, 2007.
AeroMed Software Flight Management Module Version 2.2 Reference Manual, revised Nov. 10, 1992, 177 pages.
AeroMed Software Dispatch Module Version 2.2 Reference Manual, revised Nov. 10, 1992, 150 pages.
EmsCharts, Inc.'s Preliminary Invalidity Contentions, *Golden Hour Data Systems, Inc.* v. *emsCharts, Inc., and Softtech, LLC*, U.S. District Court for the Eastern Division of Texas, Marshall Division, Civil Action No. 2:06-cv-381-TJW, Aug. 27, 2007, 22 pages.
"ww.aeromed-software.com," Feb. 5, 1998, printed on Apr. 29, 2003.

* cited by examiner

DATA ACCURACY FILTER FOR INTEGRATED EMERGENCY MEDICAL TRANSPORTATION DATABASE SYSTEM

RELATED APPLICATIONS

This application claims priority to U.S. Provisional Application No. 60/246,310, filed Nov. 6, 2000 and titled "INTEGRATED EMERGENCY MEDICAL TRANSPORTATION DATABASE SYSTEM WITH DATA ACCURACY FILTER," which is hereby incorporated by reference in its entirety. This application is related to U.S. application Ser. No. 10/007,641 entitled "COMPLIANCE AUDIT FOR INTEGRATED EMERGENCY MEDICAL TRANSPORTATION DATABASE SYSTEM," filed on even date herewith, U.S. application Ser. No. 10/007,642 entitled "BILLING MODIFIER MODULE FOR INTEGRATED EMERGENCY MEDICAL TRANSPORTATION DATABASE SYSTEM," filed on even date herewith, and U.S. application Ser. No. 09/659,886 entitled "INTEGRATED EMERGENCY MEDICAL TRANSPORTATION DATABASE AND VIRTUAL PRIVATE NETWORK SYSTEM," filed on even date herewith.

BACKGROUND OF THE INVENTION

1. Field of the Invention

This invention relates to an integrated medical database system. More specifically, this invention relates to a data accuracy filter for a medical database in the emergency medical transportation industry.

2. Description of the Related Technology

Current documentation procedures in the medical transport industry are based on an inefficient paper and pencil technology. Important information is frequently collected on loose sheets of paper. In the environment of emergency medical transport, little time is available to neatly chart and document all pertinent and required information on a single document. Dispatch data, demographic data and clinical data are normally tracked as fragmented pieces of information that are later coalesced into a complete patient chart. In many cases, these data include the same information, thus forcing the input of redundant information. The resultant chart is therefore vulnerable to being incomplete and unreliable. In a medical setting, incomplete information can lead to disastrous clinical results.

This same technology is used to support industry quality improvement and billing procedures and submit letters of transport justification. This paperwork is usually carried out well after the date the patient is encountered, prolonging account receivable times in many instances to the point of compromising and jeopardizing service compensation. Inventory stocking and tracking is similarly a victim of extended turnover times and is often incomplete and inaccurate.

The fragmentation throughout the medical transport environment is also evident in the myriad of entities throughout the country practicing different standards of care and documentation. As is the case in other segments of the healthcare industry, even seemingly simple tasks of communicating among the various entities, as well as among sections of a single providing entity, is severely hampered by the lack of a common communication format. This is especially evident when certain aspects of the system (such as computerized clinical laboratory result displays) have been upgraded with a uniquely tailored computerized system, while the remaining functions are still performed in an archaic manner. While the upgraded system may be effective for one singular aspect, such as dispatching, lab reporting, or chart dictating, the remainder of the system does not improve its effectiveness due to the other archaic components.

Automated data accuracy checking and a demographic audit capability would enhance such an integrated medical database system. Before completion of information and transmission of data, what is desired is a system that may check for completeness of billing and patient demographic information based on criteria specific to the type of transport, the type of incident, the type of patient or other relevant information or data previously collected.

SUMMARY OF CERTAIN INVENTIVE EMBODIMENTS

One aspect of the present invention is a computerized, integrated emergency medical transportation database system having a demographic audit module, the system comprising a medical emergency database configured to store clinical encounter information, patient demographic data, and transport information; and a demographic audit module in communication with the medical emergency database, wherein the demographic audit module is configured to determine whether sufficient patient demographic data exists in the medical emergency database, and search other databases in an attempt to obtain missing demographic information.

Another aspect of the invention is a method of auditing demographic data in an integrated emergency medical transportation database system, the method comprising collecting at least clinical encounter information, patient demographic data and transport information into a medical emergency database; applying modifiable data collection rules associated with a payer type to determine whether sufficient patient demographic data exists in the medical emergency database; searching other databases in an attempt to obtain missing demographic information; and recording attempts to obtain missing demographic information.

Yet another aspect of the invention is an integrated emergency medical transportation database system having a data accuracy filter module, the system comprising a medical emergency database configured to store clinical encounter information, patient demographic data, and transport information; and a data accuracy filter module in communication with the medical emergency database, wherein the data accuracy filter module is configured to determine whether sufficient patient demographic data exists in the medical emergency database, and search other databases to obtain any missing demographic information.

DETAILED DESCRIPTION OF CERTAIN INVENTIVE EMBODIMENTS

The following detailed description presents a description of certain specific embodiments of the present invention. In this description, reference is made to the drawings wherein like parts are designated with like numerals throughout.

For convenience, the discussion of the invention is organized into the following principal sections: Introduction, Hardware Overview, Data Flow Between Modules, Description of Software Module, and Conclusion.

Introduction

In certain embodiments, the present invention relates to an object oriented, interactive, international, client-server service for the medical transport industry. The service may integrate all aspects of patient record documentation into a single complete electronic chart. A server computer provides chart database information access to multiple transport providers simultaneously by securely transmitting, storing and maintaining standardized patient data, for instance, using guidelines set forth by the Scrambling Standards Organization. Individual transport-providing entities, such as helicopter and ambulance companies, obtain coded access to this server via phone lines with a modem equipped personal computer. Security is maintained by assigning each entity a unique code or identifier. Integrated Services Digital Network (ISDN) lines, Digital Satellite Systems (DSS), dedicated trunk lines (T1, T3, etc.), cable modem, DSL, or digital wireless systems may also be used for communication.

Each crew member involved in the patient's chart documentation, i.e. dispatcher, flight nurse, paramedic and physician, as well as administrator and collector, possess coded access to chart portions relevant to their responsibilities and level of care provided. The chart is then electronically generated from the compendium of the information entered in a standardized fashion and in accordance with minimum industry documentation requirements and the inventory of financial health care standards. The system provides complete and accurate chart documentation and maintains internal consistency between each separate module. Furthermore, any sentinel events are automatically referred to the appropriate, responsible party. A sentinel event is any action during the encounter that might require a further review. Examples of sentinel events are scene times exceeding 40 minutes, nonsensical or inconsistent data entry by an emergency transport crew member, supply shortages for equipment not utilized or repeated claim denials.

Billing can be submitted electronically to the appropriate party in an appropriate format that reduces the accounts receivable times for each patient encounter. Letters of justification are automatically generated as well as follow up letters and utilization review reports. Inventory reports and lists of necessary base supplies and medicines are also electronically updated to appropriate supply centers and administrators. Customized and research reports can also be provided rapidly.

Data security and an automatic backup are provided. Although the chart data is normally made the property of the respective transport service provider, the system can retain non-proprietary data to provide industry benchmarking, quality assurance analysis and clinical research opportunities. Such standardized data collection and documentation will furthermore enable the development of an Emergency Medical Services data library to assist in the justification and legislation of governmental preventive policies for public safety.

Hardware Overview

Figure 1:
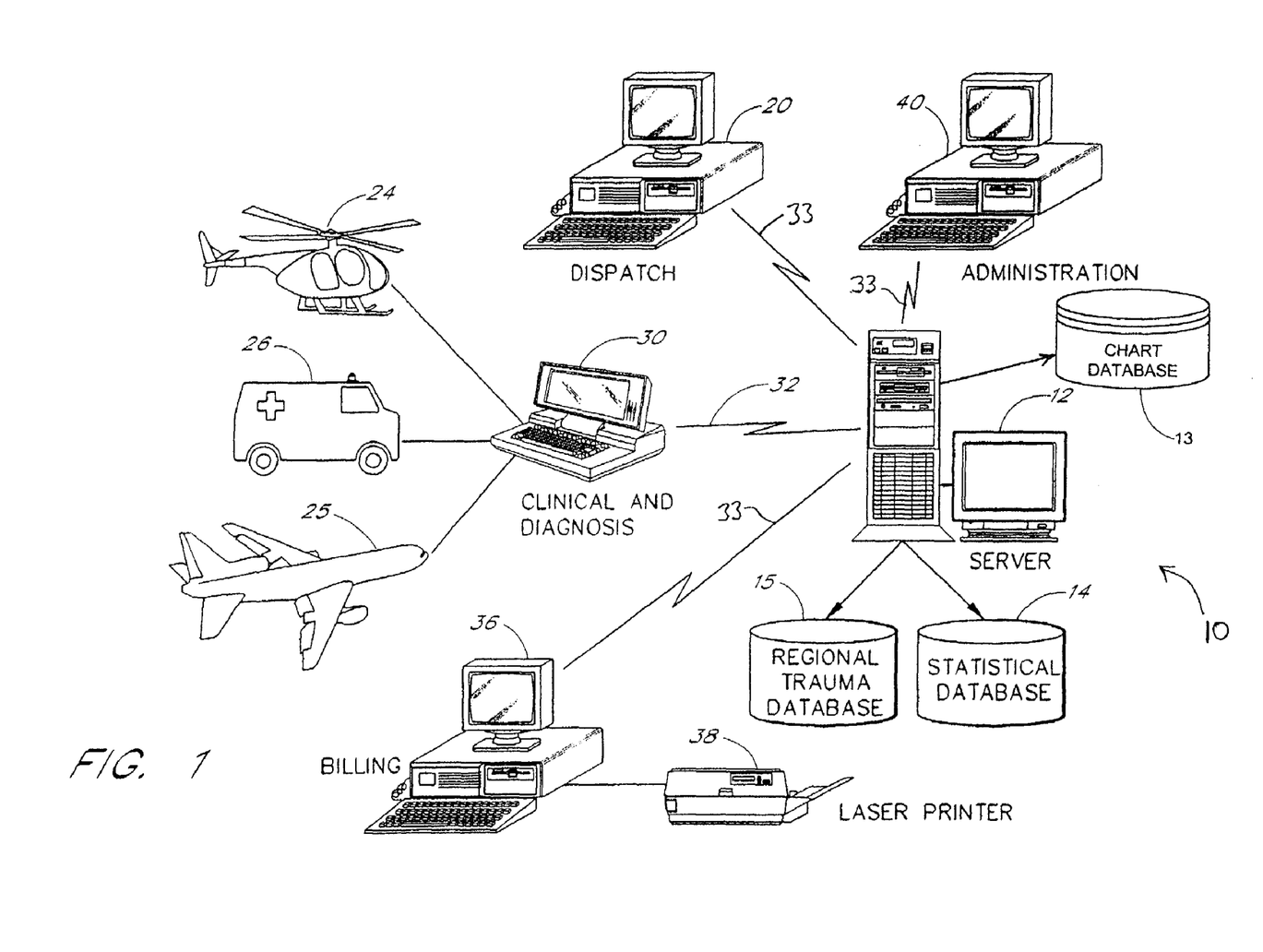
FIG. 1 is a diagram illustrating the on-line computing environment of one embodiment of the medical database system, including a dispatch interface computer, server computer, backup computer, clinical and diagnosis interface computer, administrative interface computer and billing interface computer.

FIG. 1 provides an overview of the computer hardware involved in one embodiment of the medical database system. In this embodiment, the medical database system 10 includes a server computer 12. The server computer 12 can be based on any well-known microprocessor such as those manufactured by Intel, Motorola, IBM or others. The server computer should be able to enable rapid simultaneous access to many users of the system. In one embodiment, the server computer 12 is an Intel Pentium class computer having at least 256 Megabytes of RAM and a 10 gigabyte hard disk drive and a 500 MHz processing speed. Of course, many other standard or non-standard computers may support various embodiments of the medical database system 10.

The database application may be programmed in, for instance, ACIUS's 4th Dimension (4D) language and used in conjunction with the 4D Server and Client program. Also, another alternative computer environment is Microsoft Corporation's Visual Basic language with C++ middleware, and the BackOffice SQL Server program. It can therefore run in a standard Windows/Macintosh point-and-click office environment, and requires no additional, specialized software programming from the user. Of course, other standard or non-standard computer environments may support various embodiments of the medical database system 10.

As illustrated, the server computer can access a chart database 13. The chart database 13 stores the previously described electronic charts corresponding to patients that have utilized emergency medical transportation. The server computer can also access a statistical database 14 to store and extract statistical information from data entered during patient encounters. The collected statistics might include, for example, average scene and transport times, number of transport requests per demographic region and time of year, average number of advanced procedures performed by crew members and number of complications encountered. In addition, the database 14 can hold information relating to the average length of time to process claims by category and payment plan.

The server computer can also be linked to a regional trauma database 15. The database 15 holds information relating to local trauma centers, emergency medical practice and other local trauma-related information.

The dispatch module on the server computer 12 can be accessed via an interface to a dispatch computer 20, which might reside, for example, at the dispatch center that receives the initial call to deploy an emergency medical team. The dispatch computer 20 can provide just a communications interface to the server computer 12 so that it acts as computer terminal, or it can contain a portion of the dispatch module.

Based on the scene location and needs of the patient, the dispatch center might deploy a helicopter 24, airplane 25, ambulance 26, or other transportation mechanism. The dispatch computer 20 communicates with software for collecting information on the patient encounter and scheduling and deploying a crew to assist the injured patient. Within the medical database system 10, the helicopter 24, airplane 25 or ambulance 26 would include a portable computer or computing device 30 (Note that the portable computer 30 may be any electronic device that includes computing capability.) that is used by the emergency medical team during the patient encounter. A wireless connection 32 can be made by the portable computer 30 to the server computer 12 to update the database 14 after any data has been entered. In other embodiments, other ways of communication with the server 12 can be used. The portable computer 30 can include clinical and diagnosis modules to assist the emergency medical team in treating the injured patient, or can act as a terminal to communicate with these modules on the server computer 12. As will be explained below, the clinical and diagnosis modules can help the emergency medical team determine the proper diagnosis and treatment of the patient.

The medical database system 10 also includes a billing computer 36 in communication with the server computer 12. The billing computer 36 interfaces with the server computer 12 to run the billing module for tracking charges. The software billing module can be stored directly on the billing computer 36 or, alternatively, stored on the server 12 and accessed via the billing computer 36. The billing module is used to track charges, inventory, and medical equipment. In addition, it is used during the patient encounter for providing billing functions within the medical database system 10. The billing computer 36 communicates with a laser printer 38 to provide printed reports and bills to hospitals, patients and medical centers.

An administration computer 40 interfaces with the server computer 12 to provide run administrative reports. These reports might relate to the statistical information contained in the statistical database 14. In addition, the administration computer 40 might run reports that relate to payroll, inventory, flight training or many other administrative issues.

It should be noted that the dispatch interface computer 20, portable computer 30, billing computer 36 and administration computer 40 can communicate with the server computer 12 through a variety of mechanisms, as shown by connection paths 32 and 33. For example, a wireless LAN or cellular network may connect each computer with one another. In another embodiment, dedicated or dial-up phone lines can be used to communicate between the different computers. Communication mechanisms may include networks such as the Internet and may include virtual private networks (VPNs), which are further discussed in Applicant's copending patent Application No. Ser. No. 10/012,884, entitled INTEGRATED EMERGENCY MEDICAL TRANSPORTATION DATABASE AND VIRTUAL PRIVATE NETWORK SYSTEM, and which is hereby incorporated by reference.

Data Flow Between Modules

Figure 2:
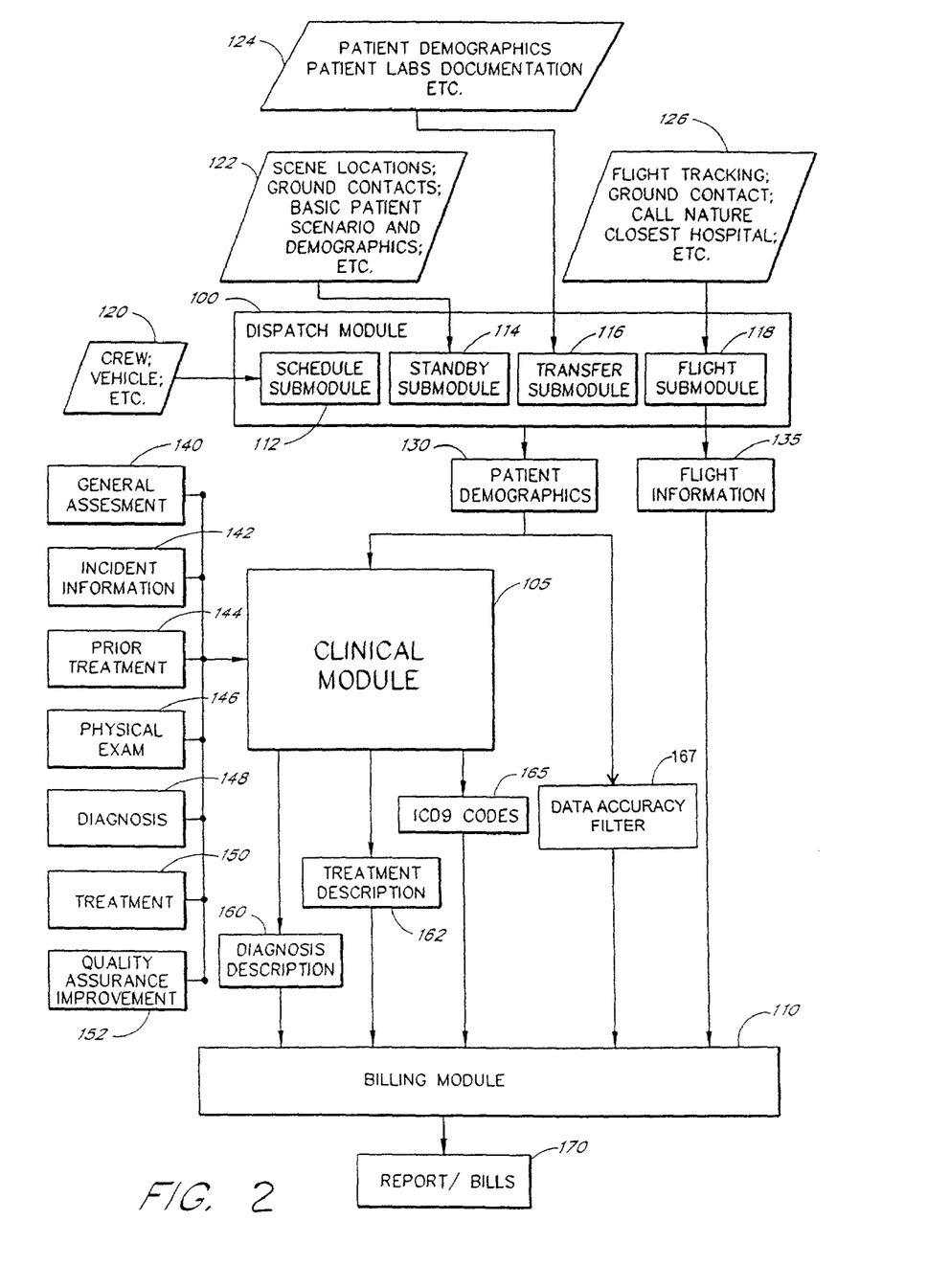
FIG. 2 is a block diagram illustrating one embodiment of the flow of data among a Dispatch module, a Clinical module, and a Billing module, in one embodiment of the medical database system.

Referring now to FIG. 2, a block diagram of one embodiment of the data flow between the various modules within the medical database system is illustrated. FIG. 2 illustrates the flow of data between a dispatch and demographic module 100 (hereafter referred to as the dispatch module), a clinical module 105 and a billing module 110. The dispatch module 100 includes a scheduling submodule 112, a standby submodule 114, a transfer submodule 116 and a flight submodule 118. These various submodules process information received into the overall dispatch module 100. For example, crew information 120 is processed within the schedule submodule 112. In addition, scene information 122 is processed within the standby submodule 114.

Patient demographics and patient clinical information 124 is processed within the transfer submodule 116. Flight tracking and other transportation information 126 is processed within the flight submodule 118. Once the various submodules within the dispatch module 100 have processed their respective information, a set of patient demographic information 130 and flight information 135 is made available to the remaining modules. For example, some of the patient demographic information 130 is imported into the clinical module 105.

In addition, many other pieces of data are placed within the clinical module 105. For example, the general assessment 140 of the patient that is taken by the emergency medical team is imported into the clinical module for further processing. In addition, other incident information 142 such as the type of incident (car accident, motorcycle accident, etc.) is sent to the clinical module 105. Prior treatment information 144 obtained from a physical exam of the patient or other information is also sent to the clinical module 105.

The prior treatment information might be important in determining whether the patient had already been treated for similar injuries thereby affecting the clinical diagnosis. Information collected from the physical exam 146 at the scene is also sent to the clinical module 105. In addition, any diagnosis 148 from the attending emergency medical team can be sent to the clinical module 105. It should be noted, as discussed below, that the medical database system 10 (FIG. 1) may also provide a diagnosis based on the physical exam information 146 and other information within the clinical module 105. This will be explained in more detail below.

Information relating to the treatment 150 of the patient is also sent to the clinical module 105. The medical database system 10 (FIG. 1) also includes a quality assurance database 152 which allows the emergency medical team to make suggestions or other comments that may be useful in additional treatments or incidents. For example, if the emergency medical team notes that a particular series of exam results has led to a unique diagnosis, this information can be input into the clinical module 105. Thus, the next time these same physical exam results are seen in a patient, the new diagnosis can be suggested to the emergency medical team.

Once the clinical module 105 has received its necessary information, data is output to the billing module 110. For example, a description of the diagnosis 160, a treatment description 162 or ICD-9 codes 165 can be sent from the clinical module 105 to the billing module 110. As is well known, ICD-9 codes are a set of unique codes referring to most well known medical procedures. These codes are used throughout the insurance industry to obtain payment for various medical procedures. In addition to the data from the clinical module 105, patient data can be obtained from the patient demographic information 130. Patient data and demographic information are processed by a data accuracy filter module 167. The processed data from the data accuracy filter module 167 can be retrieved into the billing module 110. The data accuracy filter module 167 will be described in conjunction with FIG. 3 below. The flight information 135 can also be fed into the billing module 110. The information received at the billing module 110 is then used within the billing module to generate reports and bills 170. As is to be expected, these reports and bills are sent to the various insurance companies and insurance providers. Thus, the medical database system 10 (FIG. 1) is an integrated system for providing many services within the medical industry. Further descriptions of the software modules are provided in Applicant's U.S. Pat. No. 6,117,073, which is hereby incorporated by reference.

Description of Software Module

The Data Accuracy Filter Module

Figure 3:
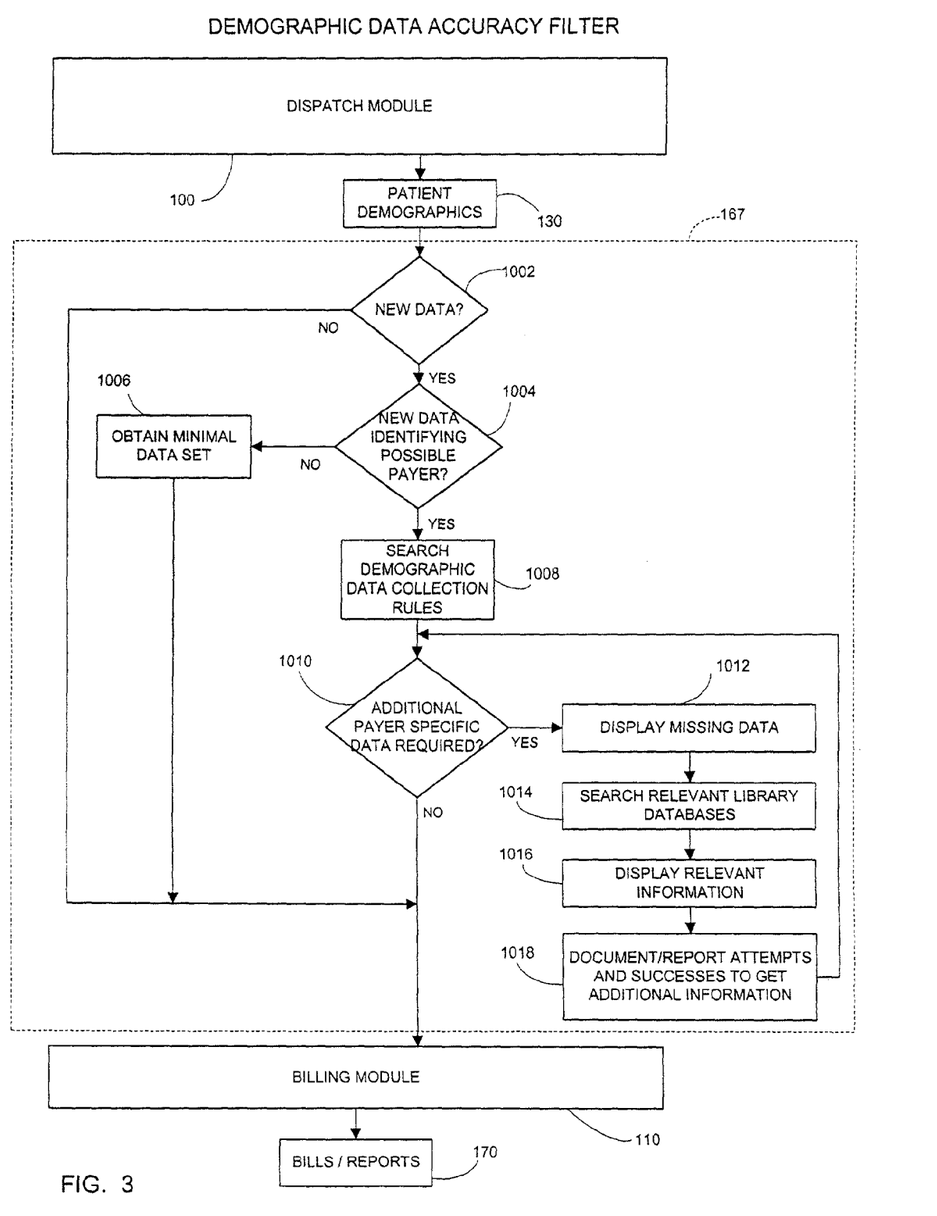
FIG. 3 is a flowchart illustrating one embodiment of the Data Accuracy Filter module process of FIG. 2.

Referring now to FIG. 3, a flowchart illustrating one embodiment of the data accuracy filter module 167 process (FIG. 2) is described. In one embodiment, the data accuracy filter module 167 is configured for use as a demographic data accuracy filter or a demographic audit filter. Before completion of information and transmission of data, demographic data accuracy filter checks for completeness of billing and patient demographic information based on criteria specific to the type of transport, the type of incident, the type of patient or other relevant information or data previously collected. The filter module process 167 prompts a user to obtain needed information and provides resources to assist users in obtaining such information immediately based on a specific library of modifiable demographic data rules. The filter module process 167 can be used to monitor the performance of individual users at collecting data and is exportable in report format.

As described above, patient and demographic data is collected at the dispatch and demographic module 100. Patient demographics data 130 is forwarded to the filter module process 167. At decision state 1002, the demographics data 130 is checked for new data and is screened for new data leading to additional payers based on a specific library of modifiable demographic data rules. If there is no new data leading to additional payers, filter module process 167 completes, and processing in the medical database system continues at the billing module 110, as described above. If it is determined at decision state 1002 that there is new data leading to additional payers, process 167 advances to a decision state 1004 based on a specific library of modifiable additional payer data rules where a determination is made whether there is any new data that identifies a possible payer type. Examples of payer types are: Medicare, Blue Cross, Medicaid, Auto, or Workers Compensation. An example of a situation where this can occur would be if the crew indicates that this is an automobile accident related injury, then the new data is sent to state 1008.

If the new data is not related to identifying possible payer types, as determined at decision state 1004, filter module process 167 moves to a state 1006 to obtain a minimal data set which is a set of data that is required on each patient to generate a bill to the patient. Examples of minimal data set members include: name, phone number, address, Social Security number. However, if the new data does identify possible payer types, as determined at decision state 1004, process 167 moves to state 1008 where a search of a set of modifiable demographic data collection rules is made to determine the type of demographic data required for the new payer type. That is, new data identifying an additional payer is filtered through the demographic data collection rules to determine if additional data elements are required. For example, if the payer type is workers compensation, the system requests the name and address of the employer, or for an automobile accident, the system searches the database and requires automobile insurance information.

Example: Demographic Data Collection Rules
If data in Dispatch module indicates Auto accident is Yes
Encourage crew member to collect the following data
Auto insurance
Law enforcement incident number
Third Party insurance information
If not present, provide contact information and encourage call and input
If crew not able to amend data request results of attempts
Track all crews activity The filter module process 167 then moves to a decision state 1010 where a determination is made whether any additional payer specific data is required. In one embodiment, this is determined by a set of rules created as the billing department learns about specific payer requirements. Examples of specific payer data that could be required include: law enforcement number for automobile related claims, or work address for workers compensation. If additional data elements are required, then these new required elements are added to a missing data list along with the minimal data set. If no further payer specific data is required, as determined at decision state 1010, process 167 completes and moves to the billing module, as described above.

Figure 4:
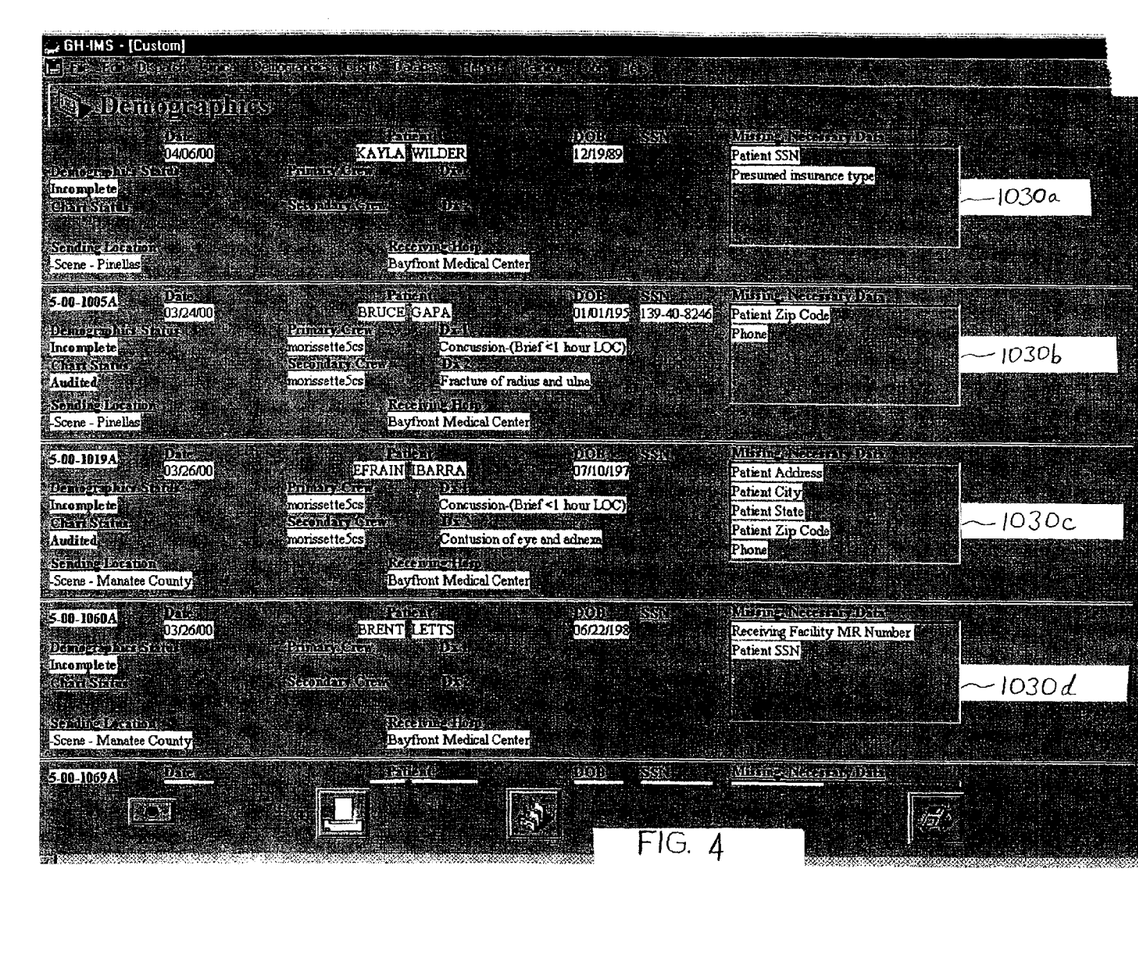
FIG. 4 is a screen display of exemplary demographic data for several patients including a Missing, Necessary field.

However, if additional payer specific data is required, as determined at decision state 1010, process 167 moves to state 1012 where any missing data for the payer is displayed. The missing data list, having the missing data elements, along with the minimal data set are displayed to the user. Referring to FIG. 4, a screen display of exemplary demographic data for several patients is shown, including a "missing, necessary data" field 1030a, 1030b, 1030c and 1030d. Once the missing data has been displayed, process 167 advances to state 1014 where a search of relevant software library databases is undertaken. That is, the missing data elements are reviewed and possible resources (contact information) for obtaining the missing information is sought from the library databases. In one embodiment, this is done by clicking on a look-up icon. Library databases are user-definable and modifiable databases that are added to the software so as to enhance its capability for an individual client. These databases can be located within the medical transportation system, or can be external databases that are accessed, for example, through the Internet or other network.

Following the search at state 1014, process 167 proceeds to state 1016 wherein any relevant information from the library database search is displayed. It should be realized that the relevant information displayed might include the actual missing data, or a pointer to a contact that could provide such data. For example, the relevant information might provide the name, address, e-mail address, telephone number, or web page of a contact that would be able to provide such data.

Once the relevant information has been displayed at state 1016, process 167 advances to state 1018 where any attempts and successes of retrieving the additional information is docketed. That is, information from the contact attempts is recorded, and reports of attempts, successes, further actions required, and failures can be captured so that additional attempts to get information do not repeat the same steps. Upon completion of state 1018, process 167 moves back to decision state 1010 to determine if additional missing data is required. If the data is complete, as determined at decision state 1010, then the electronic chart is released for billing review and bill preparation at the billing module 110.

CONCLUSION

Specific blocks, sections, devices, functions and modules may have been set forth. However, a skilled technologist will realize that there are many ways to partition the system of the present invention, and that there are many parts, components, modules or functions that may be substituted for those listed above.

As should be appreciated by a skilled technologist, the processes that are undergone by the above described software may be arbitrarily redistributed to other modules, or combined together in a single module, or made available in a shareable dynamic link library. The software may be written in any programming language such as C, C++, BASIC or Visual BASIC, Pascal, Java, and FORTRAN and executed under a well-known operating system, such as variants of Windows, Macintosh, Unix, Linux, VxWorks, or other operating system. C, C++, BASIC or Visual BASIC, Pascal, Java, and FORTRAN are industry standard programming languages for which many commercial compilers can be used to create executable code. A database programming language such as ACIUS's 4th Dimension (4D) language used in conjunction with the 4D Server and Client program may also be used.

While the invention has been described in connection with specific embodiments thereof, it will be understood that it is capable of further modification, and this application is intended to cover any variations, uses, or adaptations of the invention following, in general, the principles of the invention and including such departures from the present invention as would be understood to those in the art as equivalent and the scope and context of the present invention is to be interpreted as including such equivalents and construed in accordance with the claims appended hereto.

What is claimed is:

1. A computerized, integrated emergency medical transportation database system having a demographic audit module, the system comprising:
    a medical emergency database configured to store clinical encounter information, patient demographic data, and transport information comprising the type of transport, and wherein the patient demographic data is selected from a group consisting of: the patient name, the patient social security number, the patient insurance data, the patient address, the patient date of birth and combinations thereof; and
    a demographic audit module in communication with the medical emergency database, wherein the demographic audit module is configured to:
        determine whether sufficient patient demographic data exists in the medical emergency database, wherein the sufficient patient demographic data comprises the patient name, the patient social security number, the type of transport, and the patient insurance data,
        search other databases in an attempt to obtain missing demographic information from at least one of the other databases; and
        retrieve at least a portion of the missing demographic information from at least one of the other databases.

2. The system of claim 1, wherein the demographic audit module is additionally configured to record one or more attempts to obtain any missing demographic information.

3. The system of claim 1, wherein the demographic audit module is additionally configured to apply modifiable data collection rules associated with a payer type to determine whether sufficient patient demographic data exists in the medical emergency database.

4. The system of claim 1, additionally comprising a billing module in communication with the medical emergency database, the billing module receiving data from the demographic audit module.

5. The system of claim 1, wherein the patient demographic data comprises data specific to an insurance provider.

6. The system of claim 1, wherein the patient demographic data is based at least in part on criteria specific to the type of transport, the type of incident, or the type of patient.

7. The system of claim 1, wherein the transport information comprises information obtained about the transport after first contact by medical transport personnel.

8. The system of claim 4, wherein the billing module is configured to generate a bill based at least in part upon the data from the demographic audit module.

9. The system of claim 2, wherein the demographic audit module is additionally configured to, subsequent to the recording one or more attempts, search at least one of the other databases for at least a portion of the missing demographic information, wherein the search is based on the record of one or more attempts.

10. An integrated emergency medical transportation database system having a data accuracy filter module, the system comprising:
    a medical emergency database configured to store clinical encounter information, patient demographic data, and transport information comprising the type of transport, and wherein the patient demographic data is selected from a group consisting of: the patient name, the patient social security number, the patient insurance data, the patient address, the patient date of birth and combinations thereof; and
    a data accuracy filter module in communication with the medical emergency database, wherein the data accuracy filter module is configured to:
        determine whether sufficient patient demographic data exists in the medical emergency database, wherein the sufficient patient demographic data comprises the patient name, the patient social security number, the type of transport and the patient insurance data,
        search other databases to obtain any missing demographic information from at least one of the other databases; and
        retrieve at least a portion of the missing demographic information from at least one of the other databases.

11. The system of claim 10, wherein the data accuracy filter module is additionally configured to record one or more attempts to obtain missing demographic information.

12. The system of claim 10, wherein the data accuracy filter module is additionally configured to apply data collection rules associated with a payer type to determine whether sufficient patient demographic data exists in the medical emergency database.

13. The system of claim 10, additionally comprising a billing module in communication with the medical emergency database, the billing module receiving data from the data accuracy filter module.

14. The system of claim 11, wherein the data accuracy filter module is additionally configured to, subsequent to the recording one or more attempts, search at least one of the other databases for at least a portion of the missing demographic information, wherein the search is based on the record of one or more attempts.

* * * * *